US006984406B2

(12) United States Patent
Cho et al.

(10) Patent No.: US 6,984,406 B2
(45) Date of Patent: Jan. 10, 2006

(54) BACILLUS SP. WL-1 STRAIN PRODUCING MANNANASE

(75) Inventors: Ki-Haeng Cho, Sungnam (KR); Ki-Hong Yoon, Taejon (KR); Dae-Weon Kim, Taejon (KR); Hwa-Gyun Oh, Seoul (KR); Young-Phill Oh, Taejon (KR)

(73) Assignee: CTC BIO Inc., Seoul (KR)

( * ) Notice: Subject to any disclaimer, the term of this patent is extended or adjusted under 35 U.S.C. 154(b) by 425 days.

(21) Appl. No.: 10/311,284

(22) PCT Filed: Jun. 20, 2001

(86) PCT No.: PCT/KR01/01048

§ 371 (c)(1),
(2), (4) Date: Dec. 17, 2002

(87) PCT Pub. No.: WO01/98462

PCT Pub. Date: Dec. 27, 2001

(65) Prior Publication Data

US 2003/0190741 A1 Oct. 9, 2003

(30) Foreign Application Priority Data

Jun. 20, 2000 (KR) .............................. 2003-33822

(51) Int. Cl.
*A61K 38/46* (2006.01)
*A61K 1/165* (2006.01)
*A23L 1/03* (2006.01)

(52) U.S. Cl. .................. 426/53; 424/94.62; 426/2; 426/56; 426/63; 435/71.1; 435/71.2; 435/200; 435/252.5

(58) Field of Classification Search ............. 435/71.1, 435/71.2, 200, 252.5
See application file for complete search history.

(56) References Cited

U.S. PATENT DOCUMENTS 5,429,828 A * 7/1995 Fodge et al. ............ 426/18
5,709,894 A * 1/1998 Julien ..................... 426/53
5,783,238 A * 7/1998 Julien ..................... 426/63
5,863,574 A * 1/1999 Julien ..................... 426/53
6,245,546 B1 * 6/2001 Hansen et al. ........... 435/200
6,399,351 B1 * 6/2002 Bjørnvad et al. ........ 435/232
RE38,047 E * 3/2003 Fodge et al. ............ 426/18
6,616,953 B2 * 9/2003 Fidler et al. .............. 426/2
2002/0160080 A1 * 10/2002 Hansen et al. ............ 426/53

FOREIGN PATENT DOCUMENTS

| JP | 57-065182 | 4/1982 |
| JP | 07-274960 | 10/1995 |
| JP | 08-051975 | 2/1996 |

OTHER PUBLICATIONS

Ethier, N., et al., "Gene cloning, DNA sequencing, and expression of thermostable beta-mannanase from *Bacillus stearothermophilus*". Appl. Environ. Microbiol. Nov. 1998; 64 (11) : 4428-32 (abstract only).

el-Helow, E. R., et al., "Production of beta-mannanase by *B. subtilis* from agro-industrial by-products: screening and optimization. Mannanase from wastes." Antonie Van Leeuwenhoek Mar. 1997: 71 (3) : 189-93 (abstract only).

Mendoza, N. S., et al., "Cloning and sequencing of beta-mannanase gene from *Bacillus subtilis* NM-39". Biochim. Biophys. Acta. Apr. 13, 1995; 1243 (3) : 552-4 (abstract only).

* cited by examiner

*Primary Examiner*—Herbert J. Lilling
(74) *Attorney, Agent, or Firm*—Nath & Associates PLLC; Viviana Amzel; Lee C. Heiman

(57) ABSTRACT

The present invention relates to a *Bacillus* sp. strain producing a mannanase which is highly active in the neutral and the acidic media. The *Bacillus* sp. WL-1 strain (KCTC 0800BP), which is isolated from the soil, produces in large scale the mannanase in the culture medium containing lactose and bran, wherein the mannanase is highly active in the neutral and the acidic media so said mannanase is useful as an additive for feeds and is helpful in the decomposition of hemicellulose.

4 Claims, 2 Drawing Sheets

○: Acidity of mannanase depending on acidity
●: Acidity of mannanase depending on temperature ● : Activity of mannanase in LB medium containing galactose and wheat bran
■ : Activity of mannanase in control LB medium
○ : Growth in LB medium containing galactose and wheat bran
□ : Growth in control LB medium

BACILLUS SP. WL-1 STRAIN PRODUCING MANNANASE

TECHNICAL FIELD

The present invention relates to a novel *Bacillus* sp. WL-1 strain producing mannanase, which is highly active in the neutral and the acidic media. More specifically, the present invention relates to a method for producing in large scale mannanase which is highly active in the neutral and acidic media and thus useful as a feed additive for monogastric animals, in which method the novel *Bacillus* sp. WL-1 strain is isolated from the soil, identified and cultured.

BACKGROUND ART

Mannanase is a promising enzyme for decomposing a mannan component that constitutes hemicellulose. Hemicellulose is a constituent component of the plant cell wall containing cellulose associated with lignin and a polysaccharide most abundant in the nature next to cellulose. Hemicellulose includes mannan materials such as galactomannan and arabitogalactan contained in the seed of leguminous plants, or glucomannan and galactogluromannan of coniferous trees. The most important availability of mannanase that is included in hemicellulase together with xylanase and glucanase is saccharifying hemicellulose, which is a recyclable plant resource in the earth, into a carbon source available to organisms. But, this use of mannanase is not put into practice yet. Presently, hemicellulase is useful in industrial applications including food processing of coffee, cocoa, tea, cereal, etc. and manufacture of pulp.

When processed with hemicellulase, grains that contain hemicellulose used for foods or feeds are converted to a form adequate for foods or feeds with an improved energy yield and a deterioration of viscosity. With an increase in the energy content of foods or feeds, it is advantageous, especially for feeds, to reduce the cost for breeding of domestic animals.

Soybean proteins are used as feeds for domestic animals such as dogs, cats, pigs, fish, fowls, or the like. Although not a principal energy source, the soybean meal is an excellent protein source containing essential amino acids. About 10% of carbohydrates as an energy source in the soybean meal are galactan and pentosan. A large amount of these carbohydrates are not digested by the monogastric animals but excreted. Mannanase decomposes galactan out of the carbohydrates of the soybean meal into a low-molecular oligosaccharide or monosaccharide that can be readily digested by the unit animals.

Mannanase is produced by microorganisms such as mold or yeast fungus as well as *Bacillus subtilis, Aeromonas, Enterococcus, Pseudomonas*, and *Streptomyces*. Some higher plants or animals can produce mannanase. Microorganisms used for production of the mannanase are usually *Trichoderma* or *Aspergillus* sp. fungal strains. Fungus-originated mannanase has the maximum activity in the acidic condition. Although different by portions in the physiological condition of the digestive organs of pigs or fowls, the pH condition of the digestive organs after the small intestine affected by the mannanase is around 6.5. Accordingly, the enzyme for feed additives is composed of mannanase, which is highly active in the neutral medium, rather than the fungus-originated mannanase having a high activity in the pH range of 3.6 to 5.5.

In general, there are three known enzymes, i.e., endo-β mannanase, exo-β mannanase and β-mannosidase that participate in the complete decomposition and conversion of the mannan, which is a principal component of hemicellulose. Endo-β mannanase catalyzes at random the hydrolysis of the β-D-1,4-mannopyranosyl bonds of mannan polysaccharides having a higher polymerization degree than mannotetraose that has a mannose polymerization degree of 4. The present invention places great importance on the first enzyme, i.e., endo-β mannanase, which will be hereinafter referred to as "mannanase".

The inventors of this invention isolated from the soil a novel *Bacillus* sp. WL-1 strain that produces mannanase, which is highly active in the neutral and the acidic media, and found out that the isolated and identified *Bacillus* sp. WL-1 strain produces a lot of mannanase in a culture medium containing lactose and wheat bran.

DISCLOSURE OF INVENTION

Accordingly, an object of the present invention is to provide a novel *Bacillus* sp. WL-1 strain producing mannanase that is isolated from the soil and identified.

Another object of the present invention is to provide a method for mass production of mannanase useful for a feed additive from the novel *Bacillus* sp. WL-1 strain isolated from the soil, identified and cultured.

Still another object of the present invention is to provide the use of mannanase produced by the method as a feed additive.

To achieve the above objects of the present invention, a number of strains isolated from the soil are cultured in a plat board medium containing an acacia fruit resin to select colonies with a large digestive ring of the fruit resin and examine the mycological characteristics of the selected colonies. Subsequently, the production of mannanase by the selected colonies is measured and the availability of the mannanase as a feed additive by analyzing the ability of digesting carbohydrates contained in the soybean meal used as a feed. Hereinafter, the construction of the present invention will be described.

BRIEF DESCRIPTION OF THE DRAWINGS

Further objects and advantages of the invention can be more fully understood from the following detailed description taken in conjunction with the accompanying drawing in which.

BEST MODE FOR CARRYING OUT THE INVENTION

Figure 1:
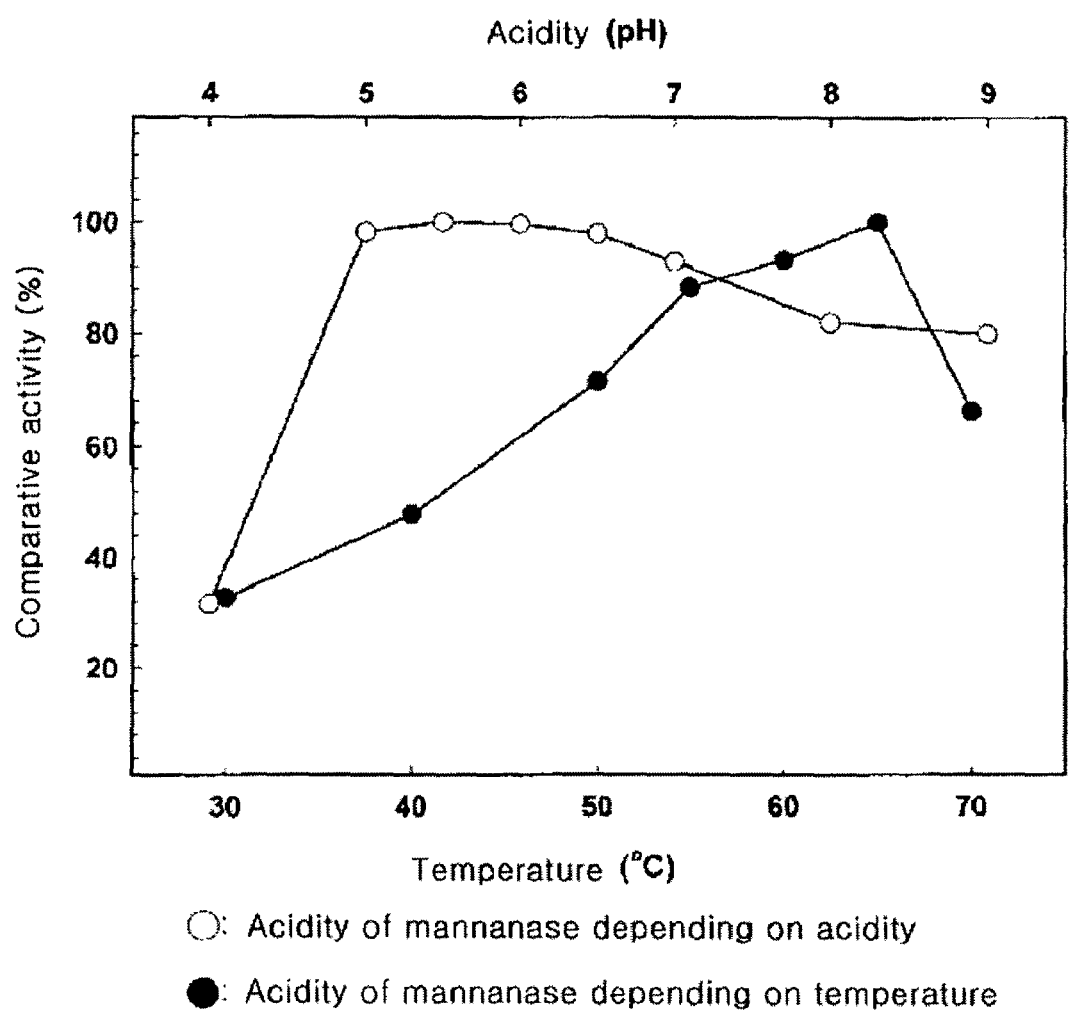
FIG. 1 is a graph showing the activity of mannanase produced by a *Bacillus* sp. WL-1 strain depending on the temperature and acidity (pH)

The present invention comprises the steps of: culturing a soil sample in an LB agar medium containing an acacia fruit resin and selecting strains with a fruit resin digestion ring formed around colonies to obtain mannanase-producing microorganisms, which strains are designated as "*Bacillus* sp. WL-1 strain"; determining the optimum growth temperature of the *Bacillus* sp. WL-1 strain and examining the morphological and physiological characteristics of the *Bacillus* sp. WL-1 strain according to the Bergy's manuals of determinative bacteriology; determining the optimum active temperature and pH of mannanase that is an enzyme produced by the *Bacillus* sp. WL-1 strain; examining the effect of the individual carbon sources on the production yield of mannanase when the *Bacillus* sp. WL-1 strain is cultured in media that are different in the content of carbon sources, i.e., galactose and wheat bran; periodically measuring the number of colonies and the activity of mannanase while culturing the *Bacillus* sp. WL-1 strain in a medium containing galactose and wheat bran as carbon sources and a medium containing no carbon source, to determine the relationship between the production yield of mannanase and the number of colonies; and treating a soybean meal with the mannanase produced by the *Bacillus* sp. WL-1 strain and measuring the increment of a reducing sugar resulting from the digestion of mannan in the soybean meal, thereby examining the availability of the mannanase produced by the *Bacillus* sp. WL-1 strain as an animal feed additive.

The LB agar medium used in the present invention contains, per 1 L of the medium, 10 g of trypton, 5 g of a yeast extract, 5 g of NaCl and 18 g of bactoagar.

Hereinafter, the present invention will be described by way of the following examples, which are not limit the scope of the present invention.

EXAMPLE 1

Isolation of Mannanase-producing Strain from Soil

To isolate a microorganism producing mannanase, 1 g of a soil sample was suspended in 10 ml of a physiological saline solution and an appropriate amount of the suspension was applied to an LB agar medium containing a 0.5% acacia fruit resin. After culturing at 37° C., colonies formed in the solid agar medium were dyed with a 0.2% Congo red solution to discriminate strains having a mannan digestion ring formed around the colonies, thereby selecting mannanase-producing strains. Finally, one strain having a highest activity of mannanase was selected and named "*Bacillus* sp. WL-1 strain".

EXAMPLE 2

Identification of *Bacillus* Sp. WL-1 Strain and Determination of Characteristics Thereof The novel *Bacillus* sp. WL-1 strain isolated from the soil in Example 1 was cultured in different temperatures to determine the optimum growth temperature. As a result, the *Bacillus* sp. WL-1 strain hardly grew at a temperature above 55° C. but showed a high growth in the temperature range from 20° C. to 50° C. In regard to the morphological and physiological characteristics as shown in Table 1, the novel strain was identified as a *Bacillus* sp. Strain according to the Bergy's manuals of determinative bacteriology. The novel *Bacillus* sp. WL-1 strain identified in the present invention was deposited with the Korean Collection for Type Cultures Gene Bank located in the Korea Advanced Institute of Science and Technology (KRIBB), #52, Oun-dong, Yusong-ku, Taejon 305–333, Republic of Korea on Jun. 7, 2000 under the Budapest Treaty and given KCTC Accession No. O800BP.

TABLE 1

Morphological and Physiological Characteristics of Bacillus Sp. WL-1 Strain.

| Div. | Response |
|---|---|
| Shape | Rodshaped |
| Endospore | + (Positive) |
| Spore shape | Oval |
| Spore position | Center |
| Motility | + |
| Gram staining | + |
| Growth temperature | 20~50° C. |
| Catalase | + |
| Oxidase | + |
| β-Galactosidase | + |
| Arginine dihydrolase | − (Negative) |
| Lysine decarboxylase | − |
| Citrate utilization | + |
| Indole production | − |
| Gelatin hydrolysis | + |
| Starch hydrolysis | + |
| Acid production from fermentation of sugars: | |
| D-glucose, D-fructose, D-mannose, Glycerol, | + |
| L-arabinose, Inositol, Mannitol, Sorbitol, | + |
| Maltose, D-xylose, galactose, Rhamnose, | + |
| Lactose, Erythritol, Gluconate | − |
| | − |

EXAMPLE 3

Response Characteristics of Mannanase Produced by *Bacillus* Sp. WL-1 Strain

The following experiment was performed to examine the activity of mannanase depending on the reaction temperature and pH in the hydrolysis of galactomannan originated from the acacia fruit resin using mannanase produced by the novel *Bacillus* sp. WL-1 strain. First, a supernatant of the culture medium was concentrated and fractioned with ammonium sulfate. The precipitate thus obtained was suspended with a 50 mM Na·phosphate buffer solution (pH 6.5) and dialyzed with the same buffer solution. Among the proteins fractioned, the fraction having the activity of mannanase was used as a coenzyme solution to measure the activity of mannanase at different temperatures and pH values. As a result, the activity of mannanase was the maximum at around 65° C. and pH 5.5 and more than 99% in the pH range of 5.5 to 7.0, which demonstrated that the mannanase produced by the novel *Bacillus* sp. WL-1 strain has a high activity at a pH value of around 7, i.e., under the physiological condition.

EXAMPLE 4

The Effect of Carbon Source on Production of Mannanase

In many cases, the production of a polysaccharase by microorganisms is affected by the carbon source contained in the culture medium. In this embodiment, a measurement was performed on the production of mannanase by the novel *Bacillus* sp. WL-1 strain depending on the addition of various carbohydrates to the culture medium. As a result, it was found out that the addition of wheat bran and galactose to the culture medium increased the production yield of mannanase. Then, an analysis was performed to determine the effect of the amount of the wheat bran and galactose on the production of mannanase by the *Bacillus* sp. WL-1 strain. First, the novel *Bacillus* sp. WL-1 strain was inoculated into a control medium that is an LB medium, and a liquid medium prepared by adding a different amount of wheat bran and galactose to the LB medium. After liquid culturing at 37° C. for 15 hours, the activity of mannanase in the supernatant was measured. As shown in Table 2, the enzyme productivity was highest in the medium containing 25% wheat bran, in which case the production yield amounted to 8.5 times that of the control medium. Also, the enzyme productivity was highest in the medium containing 1.0% galactose, in which case the production yield was 14 times that of the control medium. This revealed that the addition of galactose and wheat bran to the culture medium greatly increased the production of mannanase by the *Bacillus* sp. WL-1 strain. To measure the increase in the production of mannanase by addition of the two carbon sources, the novel *Bacillus* sp. WL-1 strain was cultured in the respective media that are prepared by adding different amounts of wheat bran to a basic LB medium containing 1.0% galactose. As shown in Table 3, the production of mannanase was highest in the culture medium containing 1.0% wheat bran, in which case the production yield was 24 times that of the control medium.

TABLE 2

The Effect of Contents of Wheat Bran and Galactose on Production of Enzyme.

| Additive | Content (%) | Activity of mannanase (unit/mL) | Comparative activity (%) |
| --- | --- | --- | --- |
| Non | | 1.9 | 100 |
| Wheat bran | 1.0 | 8.8 | 450 |
| | 1.5 | 13.6 | 693 |
| | 2.0 | 14.3 | 728 |
| | 2.5 | 16.9 | 864 |
| | 3.0 | 16.7 | 850 |
| Galactose | 0.5 | 20.6 | 1,050 |
| | 1.0 | 28.3 | 1,443 |
| | 1.5 | 22.4 | 1,143 |
| | 2.0 | 23.7 | 1,207 |
| | 2.5 | 22.8 | 1,164 |
| | 3.0 | 23.4 | 1,193 |

TABLE 3

The Effect of Mixed Addition of Wheat Bran and Galactose on Production of Enzyme.

| Additive | Content of wheat bran (%) | Activity of mannanase (unit/mL) | Comparative activity (%) |
| --- | --- | --- | --- |
| Non (LB medium) | | 1.9 | 100 |
| Wheat bran (LB medium containing 1% galactose) | 0 | 22.0 | 1,121 |
| | 0.5 | 39.9 | 2,236 |
| | 1.0 | 47.3 | 2,414 |
| | 1.5 | 43.4 | 2,214 |
| | 2.0 | 45.1 | 2,300 |

EXAMPLE 5

Figure 2:
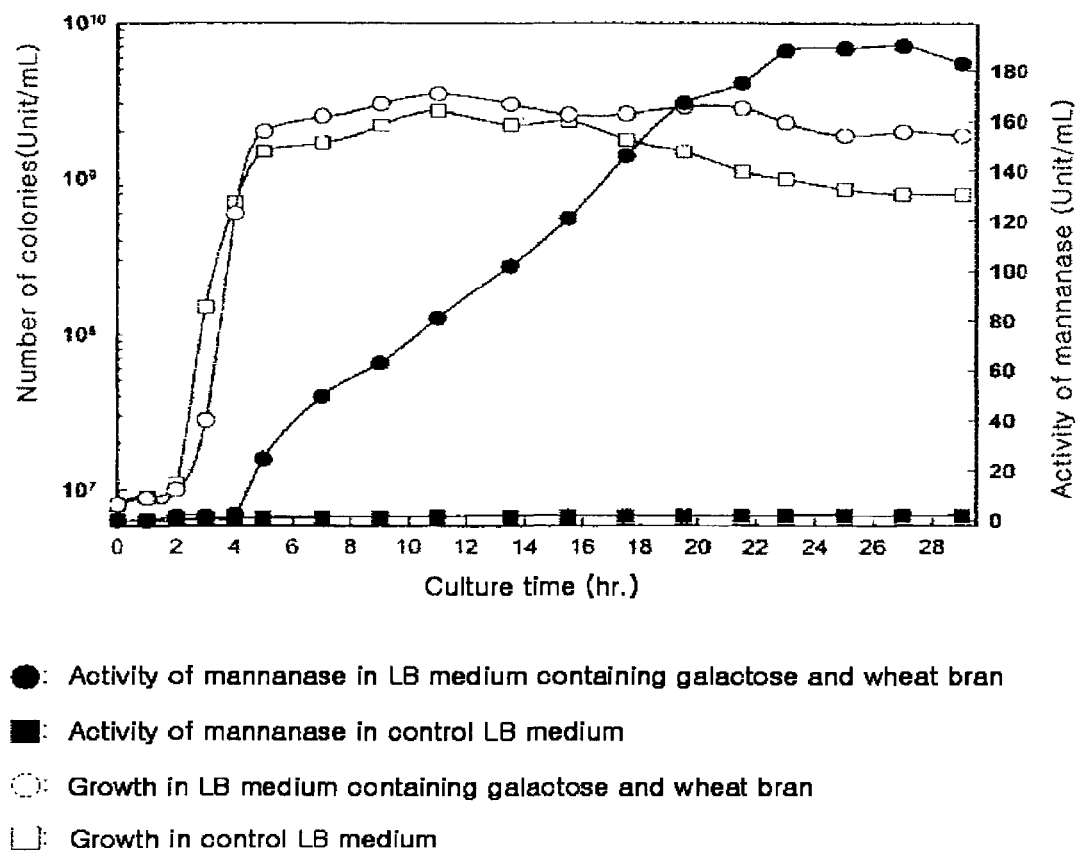
FIG. 2 is a graph showing the number of colonies and the activity of mannanase in a culture medium depending on the culture time when the *Bacillus* sp. WL-1 strain is cultured in an LB medium containing no additional carbon source and an LB medium containing 1% wheat bran and 1% galactose.

Relationship Between Increase in Production of Mannanase by *Bacillus* Sp. WL-1 Strain and the Number of Colonies Depending on Culture Time To determine the relationship between the increase in the production of mannanase due to addition of galactose and wheat bran and the number of colonies depending on the culture time, the novel *Bacillus* sp. WL-1 strain was independently inoculated into an LB medium containing no carbon source and another LB medium containing 1% galactose and 1% wheat bran and shake-cultured at 37° C. in a baffle flask. Subsequently, the number of colonies and the activity of mannanase were periodically measured. The collected culture solution was diluted and applied into an LB agar medium to count the number of colonies. The activity of mannanase in the culture medium was measured by using the supernatant of the culture medium centrifuged as a sample. As shown in FIG. 2, the *Bacillus* sp. WL-1 strain was rapidly grown in the two culture media so that the growth maintained until the stationary phase in 5 to 6 hours after the inoculation and the number of colonies was a little decreased in the LB medium after 18 hours. The production of mannanase had a wide difference between the two media. In the culture medium containing galactose and wheat bran, the activity of mannanase was continuously increased to 189 unit/mL in 24 hours with the growth of the strain and the increased culture time. Contrarily, the increase in the activity of mannanase over the culture time was insignificant in the LB medium containing no additional carbon source and the maximum activity was 2.0 unit/mL. Accordingly, the production of mannanase by the *Bacillus* sp. WL-1 strain in the medium containing 1% galactose and 1% wheat bran was increased about 95 times that in the medium containing no additional carbon source.

EXAMPLE 6

Availability of Mannanase Produced by *Bacillus* Sp. WL-1 Strain as Feed Additive To determine whether the mannanase produced by the novel *Bacillus* sp. WL-1 strain is useful as a feed additive, a soybean meal widely used as a feed additive was treated with the mannanase produced by the *Bacillus* sp. WL-1 strain and the amount of reducing sugar produced by the enzyme was measured. The *Bacillus* sp. WL-1 strain was cultured in an LB medium containing 1% galactose and 1% wheat bran and the supernatant of the culture medium was precipitated with ammonium sulfate to prepare a coenzyme solution. 40 unit/mL of mannanase was added to 1 g of the soybean meal and kept in the physiological conditions of the unit animal's small intestine, i.e., pH 6.5 and 37° C. for 6 hours. As shown in Table 4, the soybean meal was digested over the time and the amount of the reducing sugar in the solution was increased. This result showed that the mannanase produced by the *Bacillus* sp. WL-1 strain is suitable for the use purpose as a feed additive.

TABLE 4

Digestive Activity of Mannanase Produced by Bacillus sp. WL-1 Strain on Soybean Meal.

| Reaction time (hour) | The amount of reducing sugar produced after reaction ($\mu$mole) |
| --- | --- |
| 0 | 0 |
| 1 | 132 |
| 2 | 170 |
| 3 | 196 |
| 4 | 211 |
| 5 | 224 |
| 6 | 248 |

Industrial Applicability

As described above, the novel *Bacillus* sp. WL-1 strain (KCTC Accession No. 0800BP) having a mannan digesting ability that is isolated from the soil can produce mannanase in a large scale in a culture medium containing galactose and wheat bran. The mannanase produced, which has a high activity in the neutral to acidic range of acidity, is useful as a feed additive and suitable for digestion of hemicellulose in the manufacture of foods, manure and pulp. Thus the mannanase produced by the novel *Bacillus* sp. WL-1 strain is much useful in the feed, manure and paper manufacturing industries.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A *Bacillus* sp. WL-1 (KCTC Accession No. 0800BP) strain producing mannanase that is isolated from the soil.

2. A method for producing mannanase, comprising the steps:

adding 1.0 to 3.0% of wheat bran or 0.5 to 3.0% galactose to an LB agar medium containing 10 g/L of trypton, 5 g/L of a yeast extract, 5 g/L of NaCl and 18 g/L of bactoagar;

inoculating the *Bacillus* sp. WL-1 strain according to claim 1 into the culture medium; and cultivating the strain.

3. A mannanase having a mannan digesting ability originated from a *Bacillus* sp. WL-1 (KCTC Accession No. 0800BP) strain, the mannanase being prepared by the method according to claim 2 and having an activity in the pH range of 5.5 to 7.0.

4. A feed for monogastric animals containing the mannanase according to claim 3.

* * * * *

(12) EX PARTE REEXAMINATION CERTIFICATE (6080th)
United States Patent
Cho et al.

(10) Number: US 6,984,406 C1
(45) Certificate Issued: Jan. 1, 2008

(54) BACILLUS SP. WL-1 STRAIN PRODUCING MANNANASE

(75) Inventors: Ki-Haeng Cho, Sungnam (KR);
Ki-Hong Yoon, Taejon (KR);
Dae-Weon Kim, Taejon (KR);
Hwa-Gyun Oh, Seoul (KR);
Young-Phill Oh, Taejon (KR)

(73) Assignee: CTC Bio Inc., Seoul (KR)

Reexamination Request:
No. 90/007,968, Mar. 7, 2006

Reexamination Certificate for:
Patent No.: 6,984,406
Issued: Jan. 10, 2006
Appl. No.: 10/311,284
Filed: Dec. 17, 2002

(22) PCT Filed: Jun. 20, 2001

(86) PCT No.: PCT/KR01/01048
§ 371 (c)(1),
(2), (4) Date: Dec. 17, 2002

(87) PCT Pub. No.: WO01/98462
PCT Pub. Date: Dec. 27, 2001

(51) Int. Cl.
*A23L 1/03* (2006.01)
*A61K 38/46* (2006.01)

(52) U.S. Cl. .................. 426/53; 424/94.62; 426/2; 426/56; 426/63; 435/200; 435/252.5; 435/71.1; 435/71.2

(58) Field of Classification Search ............... None
See application file for complete search history.

(56) References Cited

U.S. PATENT DOCUMENTS 5,429,828 A 7/1995 Fodge et al.
5,476,775 A * 12/1995 Fodge et al. ............ 435/209
6,162,473 A 12/2000 Fodge et al.

OTHER PUBLICATIONS

Jackson, M.E., et al., "Effects of β–Mannanase in Corn–Soybean Meal Diets on Laying Hen Performance," *Poultry Science*, vol. 78, No. 12, pp. 1737–1741, Dec. 1999.

Radcliffe, J.S., et al., "The effects of Hemicell® on digestibilities of minerals, energy, and amino acids in pigs fitted with steered ileo–cecal valve cannulas and fed a low and high protein corn–soybean meal diet," *Journal of Animal Science*, vol. 77, Supplement 1, Abstracts, pp. 197–198.

Pettey, L.A., et al., "Effects of Hemicell® addition to nursery diets on growth performance of weanling pigs," *Journal of Animal Science*, vol. 77, Supplement 1, 1999, Abstracts, pp. 195.

Jackson, M.E., et al., "Effects of Hemicell® in corn–soybean meal diets with varying amino acid densities on laying hen performance," *Poultry Science*, Annual Meeting Abstracts, 88th Annual Meeting, Aug. 8–11, 1999, Springdale, Arkansas, SPSS Abstracts, S168.

James, Roger, et al., "Improved use by turkeys of corn–soy diets with beta–mannanase," *Poultry Science*, Aug. 2–5, 1998, SPSS Abstracts, S180.

Ferket, P.R., et al., "Effect of Hemicell® supplementation of Diets Containing 44% and 48% CP soybean meal on the Performance of Turkey Hens," Abstracts of Papers, vol. 76 Supplement 1, Aug. 3–6, 1997, University of Georgia, Athens, Georgia, Poultry Science Association, 86th Annual Meeting, 158.

Jackson, M.E., et al., "Effects of Hemicell® in corn–soybean meal diets on laying hen performance," Abstracts of Papers, vol. 76, Supplement 1, Aug. 3–6, 1997, University of Georgia, Athens, Georgia, Poultry Science Association, 86th Annual Meeting, 333.

* cited by examiner

*Primary Examiner*—Padmashri Ponnaluri

(57) ABSTRACT

The present invention relates to a Bacillus sp. strain producing a mannanase which is highly active in the neutral and the acidic media. The Bacillus sp. WL-1 strain (KCTC 0800BP), which is isolated from the soil, produces in large scale the mannanase in the culture medium containing lactose and bran, wherein the mannanase is highly active in the neutral and the acidic media so said mannase is useful as an additive for feeds and is helpful in the decomposition of hemicellulose.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–2 is confirmed.

Claim 3 is determined to be patentable as amended.

Claim 4, dependent on an amended claim, is determined to be patentable.

3. A mannanase having a mannan digesting ability originated from a Bacillus sp. WL-1 (KCTC Accession No. 0800BP) strain, the mannanase being prepared by the method according to claim 2 and having [an activity in the pH] *maximum activity at a pH of around 5.5 and more than 99% activity at a pH in the* range of *from* 5.5 to 7.0.

* * * * *